United States Patent
Drost et al.

[19]

[11] Patent Number: 6,126,723
[45] Date of Patent: Oct. 3, 2000

[54] MICROCOMPONENT ASSEMBLY FOR EFFICIENT CONTACTING OF FLUID

[75] Inventors: Monte K. Drost; Robert S. Wegeng, both of Richland; Michele Friedrich, Prosser, all of Wash.; William T. Hanna, Gahanna, Ohio; Charles J. Call, Pasco; Dean E. Kurath, Richland, both of Wash.

[73] Assignee: Battelle Memorial Institute, Richland, Wash.

[21] Appl. No.: 09/096,147

[22] Filed: Jun. 10, 1998

Related U.S. Application Data

[63] Continuation-in-part of application No. 08/606,155, Feb. 23, 1996, Pat. No. 5,811,062, which is a continuation-in-part of application No. 08/546,329, Oct. 20, 1995, abandoned, which is a continuation-in-part of application No. 08/282,663, Jul. 29, 1994, Pat. No. 5,611,214.

[51] Int. Cl.$^7$ .......................... B01D 53/22; B01D 53/04; B01D 53/18

[52] U.S. Cl. .................. 96/4; 96/5; 96/6; 96/9; 96/108; 96/135; 96/243

[58] Field of Search .......... 95/45–54; 96/4–14, 96/108, 135, 243, 322, 326

[56] References Cited

U.S. PATENT DOCUMENTS

| | | | |
|---|---|---|---|
| 3,396,510 | 8/1968 | Ward, III et al. | 96/5 X |
| 3,797,202 | 3/1974 | Neulander et al. | 55/158 |
| 3,823,457 | 7/1974 | Staas et al. | 29/157.3 D |
| 3,911,080 | 10/1975 | Mehl et al. | 96/12 X |
| 4,119,408 | 10/1978 | Matson | 96/5 X |
| 4,268,279 | 5/1981 | Shindo et al. | 95/46 |
| 4,516,632 | 5/1985 | Swift et al. | 165/167 |
| 4,528,003 | 7/1985 | Dittrich et al. | 96/4 |
| 4,560,394 | 12/1985 | McDonald et al. | 96/4 X |
| 4,710,205 | 12/1987 | Deetz et al. | 96/5 |
| 4,734,112 | 3/1988 | Okita et al. | 96/5 |
| 4,750,918 | 6/1988 | Sirkar | 96/5 X |
| 5,013,436 | 5/1991 | Lee et al. | 96/10 X |
| 5,135,547 | 8/1992 | Tsou et al. | 96/5 X |
| 5,281,254 | 1/1994 | Birbara et al. | 96/5 X |
| 5,290,403 | 3/1994 | Sääsk | 96/4 X |
| 5,455,401 | 10/1995 | Dumais et al. | 219/121.52 |
| 5,534,328 | 7/1996 | Ashmead et al. | 428/166 |
| 5,580,452 | 12/1996 | Lin | 96/5 X |
| 5,611,214 | 3/1997 | Wegeng et al. | 62/498 |
| 5,620,616 | 4/1997 | Anderson et al. | 219/121.52 |
| 5,700,375 | 12/1997 | Hagen et al. | 96/4 X |
| 5,788,742 | 8/1998 | Sugimoto et al. | 96/6 X |
| 5,800,596 | 9/1998 | Collin et al. | 96/4 |
| 5,811,062 | 9/1998 | Wegeng et al. | 422/129 |

FOREIGN PATENT DOCUMENTS

| | | |
|---|---|---|
| WO91/17286 | 11/1991 | WIPO . |
| WO 97/14497 | 4/1997 | WIPO . |
| WO 99/16542 | 4/1999 | WIPO . |

*Primary Examiner*—Robert H. Spitzer
*Attorney, Agent, or Firm*—Paul W. Zimmerman

[57] ABSTRACT

The present invention is a fundamental method and apparatus of a microcomponent assembly that overcomes the inherent limitations of state of the art chemical separations. The fundamental element enabling miniaturization is the porous contactor contained within a microcomponent assembly for mass transfer of a working compound from a first medium to a second medium. The porous contactor has a thickness, and a plurality of pores extending through the thickness. The pores are of a geometry cooperating with a boundary tension of one or the other or both of the media thereby preventing migration of one, other or both through the microporous contactor while permitting passage of the working compound. In the microcomponent assembly, the porous contactor is placed between a first laminate such that a first space or first microplenum is formed between the microporous contactor and the first laminate. Additionally, a cover sheet provides a second space or second plenum between the porous contactor and the cover sheet.

52 Claims, 5 Drawing Sheets

MICROCOMPONENT ASSEMBLY FOR EFFICIENT CONTACTING OF FLUID

This application is a continuation-in-part of U.S. patent application Ser. No. 08/606,155 filed Feb. 23, 1996, U.S. Pat. No. 5,811,062 which is a continuation-in-part of Ser. No. 08/546,329, filed Oct. 20, 1995, now abandoned, which is a continuation-in-part of Ser. No. 08/282,663, filed Jul. 29, 1994, now U.S. Pat. No. 5,611,214.

This invention was made with Government support under Contract DE-AC06 76RLO 1830 awarded by the U.S. Department of Energy. The Government has certain rights in the invention.

FIELD OF THE INVENTION

The present invention relates generally to a microcomponent assembly for efficient contacting of a fluid. The fluid may be liquid or gas and may contact liquid, gas or solid. The microcomponent assembly is a porous contactor in a housing forming at least one microplenum between the porous contactor and the housing. The microcomponent assembly is useful in chemical separations, especially separations involving interfacial diffusion.

DEFINITIONS

As used herein, interfacial diffusion is mass transfer across a phase boundary and includes sorption which encompasses absorption, adsorption, desorption; liquid—liquid extraction; distillation and combinations thereof. The sorption is further useful in sorption thermal machines.

As used herein, a thermal machine is defined as a device that converts heat or thermal energy to work or converts work to thermal energy or heat via a working fluid.

As used herein, boundary tension is defined as encompassing surface tension, interfacial tension and solid material strength. As generally understood, the term surface tension relates to a gas/liquid interface, interfacial tension relates to a liquid/liquid interface, and solid strength relates to a solid/gas, solid/liquid, solid/solid or combinations thereof.

As used herein adsorption includes sorption of a solute, or working compound, from a gas or a liquid into a solid.

As used herein, the term "boundary layer" refers to the "mass transport boundary layer," and is generally smaller than the corresponding boundary layers for fluid flow and heat transfer. Outside of the boundary layer, the concentration gradient for the solute, or working compound, or rate of change of concentration as a function of distance from a boundary is relatively small in comparison to the concentration gradient or rate of change of concentration within the boundary layer, and is functional for both fluids and solids.

BACKGROUND OF THE INVENTION

Interfacial diffusion of one material within another is fundamental to many chemical separation methods as well as selected energy conversion processes. Sorption processes encompass absorption, adsorption, and desorption. Sorption may be used alone or in combination with other unit operations including but not limited to heat exchange, chemical reactions, pumping, and expansions to provide chemical products, space conditioning including cooling, power generation, or combinations thereof.

Chemical Separations

Chemical separations are industrially important processes for applications including but not limited to removing impurities from or purifying material products, removing contaminants from liquid and gas streams, and separating materials for recycle or use as byproducts to a main product stream. Conventional hardware is typically very large, measurable in tens to hundreds of cubic meters in volume, thereby necessitating the application of engineering economies of scale, in large chemical processing plants, in order to provide for cost effective chemical separations.

Interfacial Diffusion Processes

Many of the most commonly used separation processes rely upon the physical phenomena of interfacial diffusion, including sorption (e.g. adsorption, absorption, desorption), distillation, liquid—liquid extraction and combinations thereof.

The process of gas absorption involves the contact of a gas with a liquid, with one or more of the constituents of the gas being absorbed within the liquid. A phase change occurs with this process, and typically considerable heat is given off (i.e., the heat of absorption). Since the solubility of the liquid is typically inversely proportional to the temperature of the liquid, this heat can be a limiting factor in the design of gas absorption units, unless methods are incorporated for removing the heat of absorption as it is generated.

Liquid—liquid extraction is similar to gas absorption, except that both mediums are liquids. Typically, one liquid is a first solvent or first medium containing a solute, or working compound which is the material to be transferred or extracted, and the second liquid or second medium is often referred to as the solvent that receives the solute or working compound. Since no phase change occurs, there is usually very little heat generated in liquid—liquid extraction processes unless another unit operation, such as a chemical reaction, also occurs.

Adsorption is much like gas absorption into a liquid, except that the gas is now sorbed within a solid media. As with gas absorption, heat is generated as the gas is adsorbed, and this can limit the rate at which gas is adsorbed unless it is promptly removed from the adsorbing media. Adsorption further includes liquid adsorption into a solid as for an ion exchange resin. Thus, fluid adsorption as used herein includes both gas adsorption and liquid adsorption.

Desorption is generally understood as the removal of a material from a liquid stream, or from a solid media, evolving it off as a gas and is the opposite of absorption or adsorption. Multiple compounds may be observed in the effluent from a desorber. For example, when ammonia is desorbed from a liquid mixture of water and ammonia, both water and ammonia are present in the gaseous effluent. Desorption can be accomplished through the addition of heat or a change in the partial pressure of the working compound within the fluid. Note that, as used herein, desorption includes the processes that are commonly called dewatering, stripping, and dehydrating.

Distillation is the separation of miscible materials based upon differences in their boiling points. It is typically performed in multiple stages, with the vapor and liquid phases flowing countercurrently and the net effect over several or many stages can be a substantial degree of separation or purity.

All of these processes involving interfacial diffusion may also involve chemical reactions, as in reactive distillation, or may involve no chemical reactions.

In general, interfacial diffusion processes involve a phase interface (gas-liquid, liquid—liquid, gas-solid, or liquid-solid), and transport of the working compound or solute across at least one fluid boundary layer. For those not including a solid, the microscopic steps that must occur include a) transport of the working compound molecules within the bulk fluid to the boundary layer, b) transport through the boundary layer to the phase interface, c) transport of the working compound molecules across the phase interface (perhaps requiring a phase change), d) transport of the working compound molecules through the boundary layer of the solvent, and e) transport of the working compound molecules away from the fluid boundary layer.

Interfacial Diffusion Equipment

Interfacial diffusion processes for the separation of bulk chemicals have traditionally been performed by the chemical process industry through the utilization of columns, with two fluids moving in opposite directions through the column. For example, liquid—liquid extraction is performed between two immiscible fluids, typically with the lighter fluid being introduced at the bottom of the column, and the heavier fluid being introduced at the top of the column. In this example, the lighter fluid will be assumed to contain the solute, i.e., the material to be extracted, and the heavier fluid will be assumed to contain a suitable solvent. In general, a high degree of solvent loading is often desired for the effluent of the column. Herein, gravity provides a motivation for fluid flow, and as the two fluids contact each other, the solute is transferred from the feed stream to the solvent.

Disadvantages associated with the equipment example include the nonuniform fluid flow characteristics of the column and the significant time that is required to allow mass transport and then reseparation (by gravity) of the two fluids. For these reasons, the designers of separation equipment typically give strong attention to the phenomenological processes at work, especially including the application of the principles of mass transport. For example, for laminar flow conditions, mass transport is due to diffusion, with the time for a molecule to move a net distance being directly proportional to the square of the distance and inversely proportional to its mass diffusivity. Likewise, the residence time for a collective amount of mass transport and sorption has the same proportionalities, and in general, the capacity of a given piece of separation equipment is inversely proportional to residence time. Hence, the designers attempt to create geometries and flow conditions such that short residence times are characteristics of the equipment, allowing high processing rates for a given hardware volume.

Short residence times for traditional interfacial diffusion separation equipment has often been obtained through either the incorporation of actuators or packings. For example, the addition of mechanical mixing equipment is commonly used within liquid—liquid extraction units to force the creation of, and intimate contact of, thin fluid streams across which mass transport would be rapid. Or, in the case of gas absorption, where the limiting transport step is often due to the much lower diffusivity of the liquid solvent, the gas may be passed through a spray of the solvent liquid, or brought in contact with a falling film of the solvent fluid. This enables the gas, or a component of the gas, to more rapidly be sorbed and transported within the fluid film.

Engineered packings likewise are used in sorption separation equipment in order to reduce mass transport times. For example, structured packings of gauze or sheet metal are often used within distillation columns, in order to improve mass transport efficiency, and a number of designs exist for types of packings. Engineered packings have been designed and applied to distillation units, liquid—liquid extraction units, and gas absorption units. Besides reducing fluid stream thicknesses, the packing also improves uniformity of fluid flow fields, so that the processing rates are optimized throughout the hardware system. However, fluid stream thickness generally exceeds the boundary layer thickness thereby retaining all transport steps described above.

In recent years, development in advanced packings have provided significant improvements in sorption unit capacities (the rate at which material is processed) and efficiencies (product purities). For example, Humphrey and Keller ("Separation Process Technology," McGraw-Hill, 1997) refer to membrane phase contactors for absorption and stripping. In these units, hollow fiber membranes are incorporated, with one fluid stream flowing within the bore of the fibers and another on the outside of the fibers. In these cases, the membranes contain random micropores, which are filled with the liquid phase, and are typically made of materials such as polypropylene. The chief resistances to mass transport for these units occur within the membrane material, where the diffusion path is torturous and subject to fouling, and external to the unit, where the diffusion lengths are significantly longer than within the hollow fibers.

In general, the performance of interfacial diffusion units for chemical separations is chiefly limited by resistances to mass transport. "Dead space" plus nonuniform flow fields, combined with long mass transport distances, cause separation equipment to typically have residence times that are characterized by minutes or hours, thereby requiring large hardware in order to provide significant production capacity. Substantial capital investment is often required because of these inherent limitations. Often, economies can be realized only through the application of economies of scale, requiring large production capacity in order to justify the inclusion of separation equipment.

For some operations (e.g., absorption, desorption, adsorption, distillation, etc.), heat transport resistances can provide performance limits as well. As can be seen from the ongoing evolution of conventional hardware, there is generally a need for efficient fluid contact, reducing heat and mass transport resistances, through short diffusion pathways, uniform fluid flow fields, resistance to fouling, and the ability to intimately add or extract heat from the sorbing media.

State of the art chemical separations tend to be more cost effective as central systems and are less cost effective on smaller scale distributed systems.

Space Conditioning Control

Chemical processes or unit operations are further used in space conditioning or climate control hardware. Microclimate control applications include but are not limited to manportable cooling and distributed space conditioning, for example 1) vehicle space conditioning; 2) distributed cooling of buildings where the use of multiple small heat pumps may eliminate the need for ducting systems, which typically wastes 50% of the cooling produced by a central cooling system; 3) lightweight air-transportable space conditioning; 4) autonomous cooling for shipping, and 5) autonomous cooling for portable containers.

In manportable cooling situations, individuals must wear protective clothing which significantly reduces heat transfer from the body. Examples include workers exposed to hazardous materials e.g. chemicals, smoke and/or radionuclides, police wearing body armor, and individuals potentially exposed to chemical or biological agents. While protective suits provide protection against hazards, they significantly decrease an individual's effectiveness. Personnel performing labor intensive tasks in a hot environment are susceptible to heat stress, especially when wearing protective clothing. The time that can be spent performing essential tasks, before succumbing to heat injury, is limited under these conditions. Supplemental cooling will permit tasks to be performed under hazardous conditions in hot climates with enhanced efficiency and reduced heat stress. Thermodynamically, a cooling cycle is the reverse of a power cycle. Although theoretically there are many thermodynamic cycles to choose from, there are three commercially prominent thermodynamic cooling cycles in use; (1) vapor-compression which requires high mechanical work input (electricity) and which is typically physically heavy because of the need for both the cooling unit and the motor (electric); heat actuated heat pumps of two sub-types, (2) absorption from and to a liquid and (3) adsorption from and to a solid. Of course, it is well understood that a thermodynamic cycle may be operated in the reverse to convert thermal energy to shaft work.

Vapor Compression Cycle

A vapor compression cycle uses a mechanical compressor to compress a working fluid in a vapor phase. The mechanical compressor may be driven by an electric motor. As the working fluid is compressed, its temperature increases. The compressed working fluid is condensed in a heat exchanger giving up heat to the surroundings and reducing the temperature of the working fluid. The cooled working fluid is decompressed through an expander which may be an expansion valve or an orifice reducing its temperature below that of the space to be cooled. The decompressed, cooled working fluid is returned to the vapor phase by receiving heat from the space to be cooled and returns to the mechanical compressor.

Although present vapor-compression cooling systems can be integrated with protective suits and distributed spaces for cooling, the present cooling systems are too heavy to carry for extended periods. Typically, a complete system sized for 4-hour operation with a cooling capacity of 350 W weighs more than 10 kg. Vapor compression cycles require significant shaft work (or electric power) for compression of the working fluid. While gains may be made by using microcomponents, for example condensers and evaporators, the overall weight and size of a vapor compression microchannel cooling system including a motor will be larger than for a sorption cycle (absorption or adsorption) for the same thermal load.

Absorption Cycle

An absorption heat pump is similar to the vapor-compression heat pump except that the mechanical compressor in the vapor compression cycle is replaced with a chemical compressor. The chemical compressor has five components; two are chemical separation units a desorber and an absorber, expander, regenerative heat exchanger and a pump. In the desorber, a mixture of fluids (circulating fluid, e.g. lithium bromide, and refrigerant, e.g. water) is heated and the refrigerant leaves the mixture as a vapor. The refrigerant is at a high pressure in the condenser and provides cooling in the evaporator after passing the expander and reducing its pressure. The reduced pressure refrigerant is absorbed back into the circulating fluid in the absorber. The absorbed mixture is pressurized by a pump and returns to the desorber, preferably through a regenerative heat exchanger. Because the mixture is a liquid, pump work is typically about $\frac{1}{100}$ of the amount of work (electricity) required to compress a vapor. Thus, the absorption cycle trades lower electricity requirement when compared to the vapor compression cycle. However, the absorption cycle does require a source of thermal energy. There are many variations of absorption cycles including but not limited to single effect, double effect, Generator/Asorber/Heat Exchanger (GAX), Diffusion Absorption and combinations thereof.

A conventional absorption cycle system relies on gravity to form falling films, which provide liquid to gas contact in the absorber and desorber. This approach has two decisive disadvantages for many portable space conditioning applications. First, the heat pump must be oriented so that the solution will fall over heat exchanger tubes and form a thin film. Deviations from the proper orientation will prevent the heat pump from working. Second, falling films have a film thickness on the order of 1 mm preventing effective mass transfer via diffusion and resulting in a physically large absorber and desorber. For distributed space cooling, weight is not as significant a factor as for manportable cooling, but for vehicle cooling including transportation containers and aircraft, weight reduction is an important consideration.

Although the absorption and vapor compression cycles differ in the way compression is provided, both systems take the same approach to heat absorption and rejection. In both cycles, superheated refrigerant enters the condensing heat exchanger, where it undergoes constant-pressure heat rejection. The resulting condensate or mixture of condensate and vapor is then adiabatically expanded through either a throttling valve or a capillary. The mixture is then routed to an evaporating heat exchanger for constant-pressure heat absorption. Compression is accomplished in the absorption heat pump system with a through single effect thermochemical compressor or desiccator consisting of an absorber, a solution pump, a regenerative heat exchanger, and a desorber (gas generator).

Absorption cycles may be grouped based on the fluid combination and on cycle arrangements. The most widely used fluid combinations are lithium bromide (LiBr) and water, where water is the refrigerant; and water and ammonia ($NH_3$), where ammonia is the refrigerant. Cycle arrangements include the single-effect cycle described above to progressively more efficient but complicated multiple effects, for example a double-effect cycle.

The single-effect $LiBr/H_2O$ cycle requires a low pressure solution pump (approx. 41 kPa (6 psi) pressure rise), but the cycle is less efficient than the double-effect cycle. While more efficient, the double-effect $LiBr/H_2O$ cycle requires a higher pressure pump (approx. 410 kPa (60 psi) pressure rise) and is more complicated than the single-effect cycle. The pressure rise required for a $H_2O/NH_3$ solution pump (2400 kPa, 350 psi) is too high for currently available small pumps and results in a heavy and inefficient system. Thus, both the single-effect and the double-effect $LiBr/H_2O$ absorption cycles are preferred candidates for cooling applications where weight and size are key issues. The $H_2O/NH_3$ system is needed in cases requiring both heating and cooling or requiring cooling below 0° C. (32° F.).

A microchannel condenser and evaporator has been demonstrated by Cuta, J. M., C. E. McDonald, and A. Shekarriz. 1996. "Forced Convection Heat Transfer in Parallel Channel Array Microchannel Heat Exchangers." *Advances in Energy Efficiency, Heat/Mass Transfer Enhancement* PID-Vol. 2HTD-Vol. 338, American Society of Mechanical Engineering, New York, also in U.S. Pat. No. 5,611,214 both herein incorporated by reference. Briefly, the microchannel condenser consists of an array of microchannels with channel widths between 100 and 300 microns and channel depths up to 1 mm. Heat transfer rates in excess of 30 W/cm$^2$ were attained with a small temperature difference and low pressure drop. The microchannel evaporator also consists of an array of microchannels with channel widths between 100 and 300 microns and channel depths up to 1 mm. Results show that convective heat transfer coefficients of 1.0 to 2.0 W/cm$^2$-K are readily attainable, and heat transfer rates up to 100 W/cm² can be obtained with a small temperature difference. These heat transfer coefficients and rates exceed those of conventional evaporators by a factor of 4 to 6. Pressure drop is typically less than 6 kPa (1 psi).

Absorption systems require a heat source for the desorber. Drost, M. K. C. J. Call, J. M. Cuta, and R. S. Wegeng. 1996. "Microchannel Integrated Evaporator/Combustor Thermal Processes." Presented at 2nd U.S. Japan Seminar in Molecular and Microscale Transport Phenomena, August 8–10, Santa Barbara, Calif., and U.S. application Ser. No. 08/883,643, both incorporated by reference herein. The microchannel combustor produces thermal energy at a rate of at least 30 W/cm², with a thermal efficiency between 82 and 85%.

Absorption system efficiency is increased with a regenerative heat exchanger, wherein no phase change occurs for the working fluid or the heat transfer fluid. Non-phase change microchannel heat transfer is well known, for example Ravigururajan, T. S., J. Cuta, C. McDonald and M. K. Drost. 1995. "Single Phase Flow Thermal Performance of a Parallel Micro-Channel Heat Exchanger," Presented at American Society of Mechanical Engineers 1995 National Heat Transfer Conference. Microchannels with channel widths between 100 and 300 microns and channel depths up to 1 mm provide single-phase microchannel heat transfer convective heat transfer coefficients of 1.0 to 1.2 W/cm²-K. These heat transfer coefficients exceed conventional regenerative heat exchanger performance by a factor of 3 to 6.

Adsorption Cycle

Adsorption cycle systems rely on the adsorption of a refrigerant into a solid to provide heat pumping. A typical system would contain two pressure vessels filled with the adsorbent. The adsorbent in one vessel has adsorbed a refrigerant. When that vessel is heated the refrigerant is desorbed from the solid adsorbent at a high pressure, the refrigerant is cooled to ambient temperature and then passes through an expander (orifice or expansion valve) where the pressure (and consequently temperature) of the refrigerant is reduced. Thermal energy is then transferred from the cooled space to the refrigerant and the refrigerant is then adsorbed in the adsorbent in the second pressure vessel. The second vessel is cooled to remove the heat of adsorption and to maintain a low pressure. This continues until the entire inventory of refrigerant has left the first tank and is adsorbed in the second tank. At this point the process is reversed and the second tank is heated, driving off the refrigerant which provides cooling and is returned to the first tank. There are many variations on the adsorption cycle and a wide range of materials has been investigated for adsorbents and refrigerants. However, all of these systems rely on adsorption in one form or another. While the adsorption cycle has been extensively investigated in both the U.S. and in foreign countries the concept has had practically no impact and there are few commercially available systems. Problems with adsorption systems include difficulty in adding or removing thermal energy from the adsorbent, the large inventory of adsorbent required and degradation of the adsorbent by repeated cycling.

Need

There exists a need for a fundamental method and apparatus that would overcome the inherent heat and/or mass transport limitations of state of the art chemical separations and cooling systems that would permit more compact distributed chemical separations and permit man-portable cooling systems.

SUMMARY OF THE INVENTION

The present invention is a fundamental method and apparatus of a microporous contactor assembly that overcomes the inherent heat and/or mass transport limitations of state of the art chemical separations.

For chemical separations, a porous contactor is used with a microplenum on at least one side of the porous contactor, to provide for substantial improvements in mass transport, thereby providing shortened residence times and higher processing rates for a fixed hardware volume. A microplenum is herein defined as a plenum having a cross section height or thickness that is less than or equal to a mass transfer boundary layer thickness. This provides the advantage of eliminating mass transport to and from the mass transfer boundary layer from a bulk volume, thereby reducing the volume of the hardware by reducing the amount of "dead volume" that does not contribute to the separation process. Compared to conventional separation hardware, a substantial hardware volume reduction is obtained (typically one to two orders of magnitude). Either a solid or a liquid or both is present in a microplenum.

For a liquid, boundary layer is well understood to be that layer in contact with a boundary or surface wherein a parametric spatial gradient exists. The parametric spatial gradient may be temperature, velocity, concentration or combinations thereof. Outside the boundary layer is considered bulk or bulk flow wherein the parametric spatial gradient is substantially zero, or, in other words, wherein the parameter is substantially constant with position. A mass transfer boundary layer is for the concentration parameter.

For a solid, especially a solid confined behind a porous contactor, it is necessary that the solid be surrounded by stagnant or non-flowing fluid. Thus, adsorption and desorption occur by interfacial diffusion between the solid and the fluid and by direct diffusion through the fluid through the porous contactor and into the fluid flowing through the plenum opposite the solid. In this case, the mass transfer boundary layer is a composite mass transfer boundary layer. Hence, the thickness of a mass transfer boundary layer, and thus the depth of the microplenum, for an adsorbent material is determined by considering the "effective mass transport boundary layer" which is a combination of the mass diffusivity of the solid and the mass diffusivity of the fluid, rather than considering only the mass diffusivity of either the solid adsorbent or the fluid alone.

A preferred embodiment includes the porous contactor fabricated as a microporous contactor using micromachining techniques, yielding micropores that are extremely precise, with essentially no torturosity. This results in a microporous contactor with low resistance to diffusive mass transport and which is additionally resistant to fouling.

A number of chemical separation units relying on interfacial diffusion are enabled by the porous contactor assembly. These include units for absorption, adsorption, liquid—liquid extraction, desorption, and distillation, including multiple stages. Besides providing for contact of the two media, the porous contactor unit additionally provides a barrier to momentum transport, allowing counterflow operation where it is advantageous, e.g., counterflow liquid—liquid extraction, thereby reducing the need for multiple stages of contactors.

Where the separation process entails two fluids with similar or low mass diffusivities, for example, two immiscible liquids, the pores are micropores of a size ranging from about 1 micron to about 30 microns, and the unit is assembled with microplenums on each side of the microporous contactor, thereby providing a stable location for the phase interface within the micropores, and effecting a high degree of separation within a compact hardware volume. In addition, when a substantial degree of heat is generated or needed to facilitate the separation process, as in gas absorption, adsorption, desorption, or distillation, the unit can be brought into intimate contact with or manufactured with integral, engineered microchannel heat exchangers so that a high rate of separation can again be realized by a compact hardware unit.

In many cases, it may be desirable to engage two separation processes in series, such as an absorption unit to purify a gas stream, and a desorber in order to remove the captured gas, allowing the solvent to be recirculated to the absorber. If a pump is included, this system becomes a thermochemical compressor, evolving the effluent gas at a higher pressure than it was absorbed at. This could alternately be accomplished with adsorption units in place of the absorption unit. Both temperature variations and pressure variations absorption/adsorption are enabled in this manner. Likewise, it may be desirable to combine a liquid—liquid extraction unit with another separation unit, again allowing for recirculation of the solvent.

There are a number of chemical separation applications for the porous contactor assembly. For example, significant research is underway to develop fuel processing systems for fuel-cell-powered automobiles. One of the needs for the automotive fuel processing system is the removal of catalyst poisons (e.g., hydrogen sulfide, carbon monoxide and combinations thereof) from the fuel stream so that it does not degrade the performance of the fuel cell or other onboard catalytic reactors for fuel processing. Onboard gas absorption or adsorption units can provide this function, because they can be made small compared to the processing rates required.

Another application is the capture of carbon dioxide from the production of fossil fuels on offshore platforms. If carbon dioxide emissions to the atmosphere are to be reduced, in order to reduce the risk of global warming, it may eventually be necessary to sequester the $CO_2$ in the deep ocean, or in the same (or similar) geologic strata from whence the fossil fuel was obtained. $CO_2$ injection is in fact a common method to increase oil field production yields. Currently, conventional separation units cannot reasonably be placed on the small space available on offshore oil platforms, and there is therefore a need for extremely compact gas separation units that can nevertheless process large quantities of material.

For cooling, the porous contactor is used in combination with heat exchangers and pumps to make a microchannel sorption thermal machine for microclimate control, preferably in the form of either a miniature absorption heat pump, or a miniature adsorption heat pump. The microchannel sorption thermal machine of the present invention is compact and could conceivably be as small as a sugar cube. This would permit a system to be used for cooling electronic components. In larger sizes the system is useful for distributed space conditioning (heating or cooling) specifically where weight is a main concern for example in manportable applications, automotive, aerospace or other transport container distributed space conditioning applications.

Absorption Heat Pump

A miniature absorption heat pump, for example may be sized to provide 350 W cooling, with dimensions of 9 cm×9 cm×6 cm, weighing approximately 0.65 kg. Compared to a macroscale absorption heat pump, this represents reduction in volume by a factor of 60. A complete microcomponent cooling system including the heat pump, an air-cooled heat exchanger, batteries, and fuel is estimated to weigh between 4 and 5 kg, compared to the 10 kg weight of alternative systems. Size and weight reductions are obtained by developing a device that can simultaneously take advantage of the high heat and mass transfer rates attainable in microscale structures while being large enough to allow efficient work to energy conversion (i.e., electric powered pumping). The reduced weight and size is made possible by using microchannel heat exchangers typically having heat transfer coefficients that exceed 2 W/cm$^2$-K and, microporous contactor assemblies having very high rates of heat and mass transfer in microscale absorbers, desorbers, rectifiers and analyzers. Typically, the size and weight of microscale components and systems can be reduced by a factor of about 1 to about 2 orders of magnitude when compared to a macroscale device with the same performance.

The device will be preferably driven by thermal energy. The thermal energy may be from any source for example the combustion of liquid hydrocarbon fuels. The energy storage density of liquid fuels exceeds the energy storage density attainable in conventional batteries by a factor of 130 (13,000 watts thermal, $W_t$/kg) for liquid hydrocarbon fuel compared to 100 watts electric ($W_e$/kg) for batteries). An absorption cooling system still requires electric power to operate a liquid pump and fan, but its overall electric power requirements are approximately an order of magnitude lower than for a conventional vapor compression system. The combination of reduced demand for electric power and the use of liquid fuels significantly reduces the weight of the absorption energy source, compared to cooling schemes that require significant shaft work, such as a vapor compression cycle.

The miniature absorption heat pump depends on the extraordinarily high heat and mass transfer rates available in microstructures to radically reduce its size while maintaining cooling capacity and efficiency. Its performance ultimately depends on microstructure with individual features as small as 1 micron. The heat pump is a miniature device, but is sufficiently large to use a small but conventional solution pump.

These device characteristics are a compelling example of the advantage of devices in the miniature size range. The specific cooling (cooling per unit volume) of the miniature heat pump is higher than that of a conventional macroscopic absorption heat pump by a factor of 60 (1.25 W/cm$^3$ compared to 0.02 W/cm$^3$) for a macroscale device. The absorption heat pump also requires considerably less electric power than a vapor compression heat pump (10 W compared to 120 W). This will reduce the need for manportable power generation or batteries for powering microclimate control systems.

Heat pump cycles including but not limited to Single effect, double effect, Generator/Absorber/Heat Exchanger (GAX) cycle and Diffusion Absorption cycle may use the microporous contactor unit.

Adsorption Heat Pump

A disadvantage of adsorption cycle systems is overcome by the use of a porous contactor and a thin adsorbent (microplenum) permitting rapid mass transfer to and from the adsorbent. Even when the adsorbent crumbles after repeated cycling, it is contained by the porous contactor. Rapid is defined as an order of magnitude reduction in time because the sorption time is proportional to the inverse of the square of the sorbent thickness. Thus, a factor of ten reduction in sorbent thickness achievable in the present invention provides a factor of 100 reduction in sorption time compared to the prior art. In addition, the availability of microvalves with very high cycling rates permits rapid cycling of the adsorbent. The present invention therefore uses 1) microstructures to improve heat transfer, 2) microstructures to reduce the impact of adsorbent degradation, 3) microactuators and valves to permit very high cycling rates and 4) small microstructures and small adsorbent volumes to reduce losses due to thermal inertia (repeated heating and cooling of adsorbent and pressure vessels).

An adsorber that is rapidly cycled is an important aspect of the present invention permitting small size with high efficiency. Rapid cycling is achieved by using an adsorber material with a thin cross section and encasing it between sheets forming a microplenum, wherein one of the sheets is porous or perforated, for example a porous contactor so that the adsorber material is contained even upon structural failure or crumbling of the adsorber material. Thin films of adsorbent in combination with microchannel heat exchangers achieve rapid heating and cooling of the adsorbent. Microchannel heat exchangers are also used for refrigerant heating and cooling.

Because the mass diffusivity within a solid adsorbent is substantially lower than the mass diffusivity within a fluid (liquid or gas), it is preferable to structure the adsorbent material such that the fluid contacts a large portion of the solid adsorbent. For example, the solid adsorbent may be shaped in the form of small spheres or other repetitive or random unit structures, and may be packed within the microplenum so that fluid can surround the structures. Note, however, that the fluid surrounding the structures is stagnant or non-flowing so that mass transfer from the solid structures to the fluid and through the porous contactor is by diffusion. For such instances, the effective mass transport boundary layer is greatly increased, approaching that of the mass transport boundary layer within the fluid.

The present invention also includes reversal of the thermodynamic cycle to achieve a conversion of thermal energy to shaft work wherein a sorption cycle is used to pressurize a working fluid that is then expanded through a work extractor (turbine or piston).

Objects

It is an object of the present invention to provide a microcomponent assembly for efficient contacting of a fluid.

It is yet another object of the present invention to provide a mechanically constrained thin film adsorber, desorber, rectifier or analyzer.

It is another object of the present invention to provide compact chemical separation units, employing interfacial diffusion.

It is another object of the present invention to provide a distributed chemical separator.

It is an object of the present invention to provide a microchannel sorption thermal machine.

It is a further object of the present invention to provide a lightweight portable cooling machine.

It is another object of the present invention to provide lightweight sorption heat pumps.

It is a further object of the present invention to use high frequency microvalves for rapid cycling of the adsorbent.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The microcomponent assembly of the present invention is a porous contactor placed in a housing that provides at least one microplenum between the porous contactor and the housing.

In chemical separations, the porous contactor or the porous membrane, having a plurality of pores extending through the thickness, is selected so that the pores cooperate with a boundary tension of one or the other or both of a first medium and a second medium preventing migration of the one, the other or the both through the porous contactor and permitting passage of a solute or working compound.

Thus, for example in an aqueous lithium bromide system, the absorber receives a water vapor as the first medium (non-wetting) and receives a solution of lithium bromide in water as the second medium (wetting) with the working compound as the water. In a solid sorption adsorber, the first medium is the solid sorbent, the second medium is the gas carrier and the working compound is the sorbed or desorbed compound.

Porous Contactor

The porous contactor 100 (FIG. 1a, FIG. 1b) is a porous or perforated material, wherein the term "microporous material" refers to material through which diffusion occurs but bulk flow or "weeping" flow is prevented. When the pores or holes are of a size to permit bulk flow or weeping, the material is referred to herein as a perforated material. A perforated material may be used for mixing two streams. The term "porous" includes both microporous and perforated. The porous or perforated material is a solid material or has a solid material thereon. In a porous material, pores 102 or holes may be either straight through the thickness or not straight as interconnected porosity.

Figures 1A, 1B:
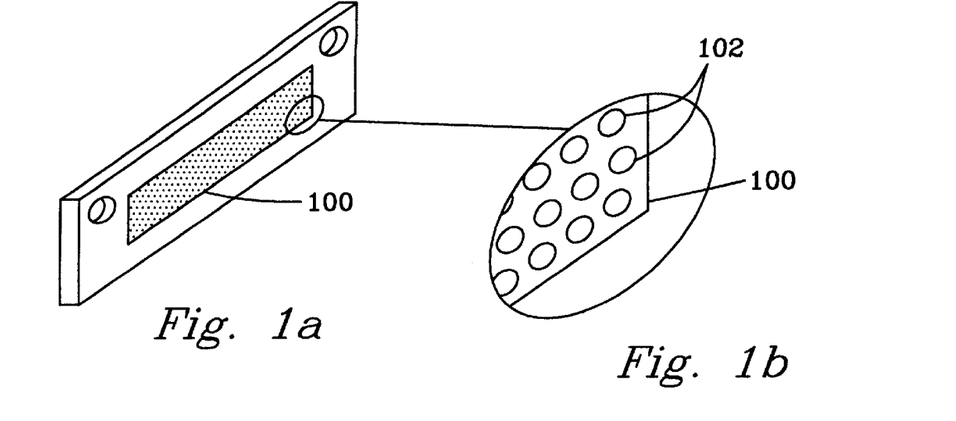
FIG. 1a is an isometric view of an outer thin sheet with a microporous contactor integral thereto.
FIG. 1b is a magnified view of the microporous contactor.

The microporous contactor 100 may be made by micromachining a metal, ceramic or plastic by, for example LiGA (Lithography, Galvanoformung (electrodeposition), Abformung (injection molding)), laser micromachining, or electrochemical micromachining. Advantages of micromachined microporous contactors include precise control of the pore size throughout the microporous contactor. Sintering produces random pore geometry and orientation.

The porous contactor 100 may be combined with active microcomponents, for example micro-actuators for imparting motion to a fluid, thereby increasing mass transport rates.

For absorption (liquid-gas), or for liquid—liquid extraction, the microporous contactor 100 is selected so that a first medium or solvent does not wet the microporous contactor but a second medium or solvent wets the microporous contactor and the working compound transfers between the first and second media and through the microporous contactor. Pore geometry is selected so that boundary tension of one or the other or both of the media prevents it from passing through the pores. Pore geometry is both size (e.g. diameter or cross sectional area) and shape (e.g. circular, polygonal including regular polygon and irregular polygon, e.g. slit, cross) of the pore. Thus, the pore geometry may not exceed that which prevents breakthrough or bulk flow of the non-wetting fluid. It is preferred that the pores have substantially the same geometry for maximum diffusion. Hence, a microporous contactor does not permit weeping or bulk flow therethrough of the solvent or medium. Preferably, the pore geometry is as large as possible and still prevent breakthrough of the non-wetting medium. For example the pore geometry for a liquid or solid may be circular holes with diameters from the limit of micromachining capability ( i.e. from about 1 microns) to about 30 microns. The small pore size provides a strong resistance to a through-sheet velocity or pressure gradient. In liquid—liquid solvent extraction, one or both solvents may enter the micropores. However, the interfacial tension at the contact within the pores prevents solvent mixing and permits a solute to transfer therebetween.

Figure 2:
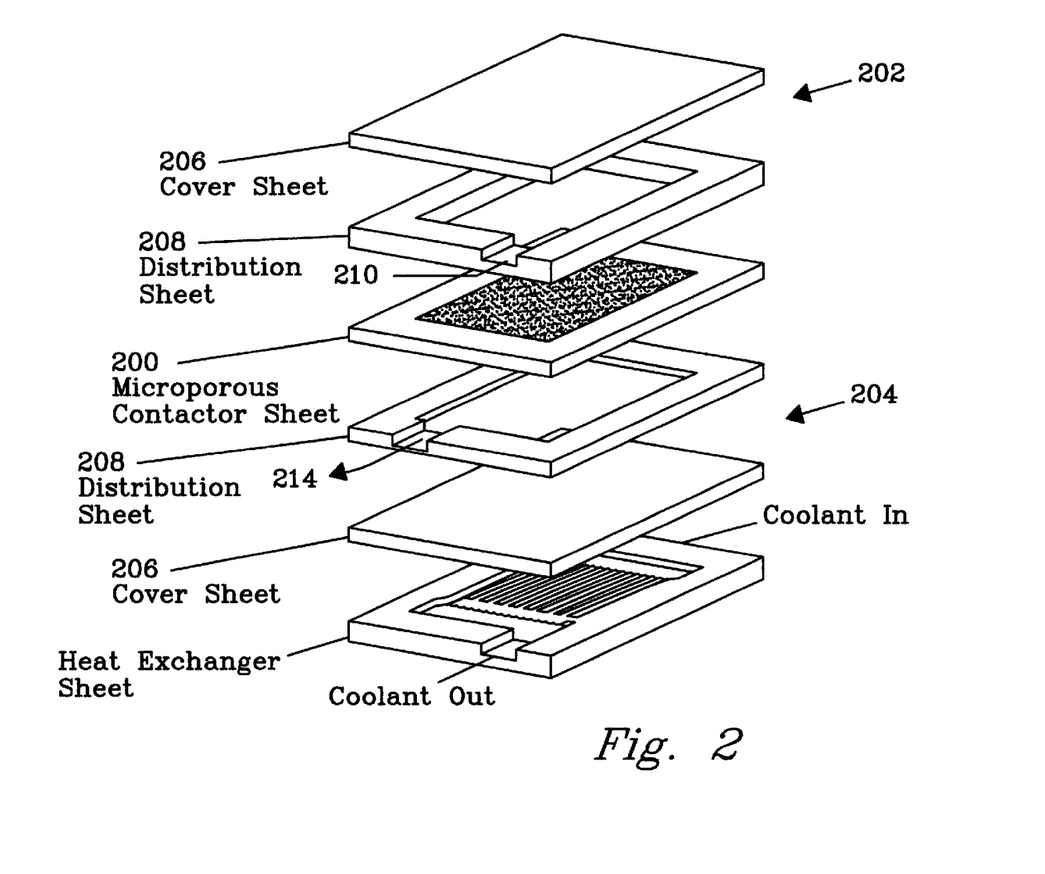
FIG. 2 is an exploded view of a liquid/gas sorber with a microporous contactor.

Because the thickness of the microplenum is less than a mass transfer boundary layer thickness of liquid or solid, the time for the working compound to substantially completely transfer from one medium to the other is substantially reduced compared to state of the art sorption. The residence time is proportional to the square of the fluid thickness (plenum depth) and inversely proportional to fluid diffusivity. Therefore, the depth(s) or thickness(es) of the solvent flow path(s) is made small, from about 1 micron to about 300 micron for a liquid or solid and up to about a millimeter for a gas. Because of the enhanced mass transfer rates, residence time is substantially reduced compared to conventional systems. A microporous contactor unit is a microporous contactor sheet as shown in FIG. 2 placed between cover sheets or laminates. Each cover sheet or laminate has or defines a microplenum between the microporous contactor sheet and the laminate or at least one microcomponent together with an inlet and an outlet permitting fluid flow across but not through the microporous contactor sheet. Mass diffusion then occurs through the microporous contactor sheet.

Micro-components, for example microgrooves, may be manufactured on one or both sides of the microporous contactor sheet. Additionally, the microporous contactor sheet may have no microcomponents itself, but the cover sheet(s) or laminate(s) may have microcomponents for directing fluid flow across the microporous contactor sheet. A further embodiment is simply a fluid microplenum on either side of the microporous contactor sheet.

In operation, fluids as solvents or media may flow in parallel, counterflow, or crossflow. The parallel flow results in lesser mass flux or extraction, but permits lesser pressure differential or gradient across the microporous contactor. When gas is one of the fluids and the gas or a constituent of the gas is to be absorbed into a liquid, it is preferred that the gas or the constituent of the gas pass through the microporous contactor, but that the liquid does not pass through the microporous contactor. Accordingly, it is preferred that the microporous contactor either be coated so that the liquid does not wet the microporous contactor or has pores sufficiently small so that the liquid is supported by its boundary tension and does not flow through the pores.

In the case wherein a microporous contactor is not sufficiently self-supporting between the covers, the covers may be made with projections or lands for support of the microporous contactor. Alternatively, as previously discussed, the microporous contactor may have grooves or microcomponents. In either case, projections or lands would support the microporous contactor.

In many practical systems, to achieve high absorption/desorption rates, heat may need to be transferred either to or from the absorption/desorption fluids. Accordingly, heat transfer, preferably with a microchannel heat exchanger, may be combined with the microporous contactor unit.

A microporous contactor unit is shown in FIG. 2. A microporous contactor 200 is placed between two covers 202, 204 each having an end block 206 and an inner thin sheet 208 that create microplena between the microporous contactor 200 and the end blocks 206 upon assembly. Note in this embodiment, the inlet and outlet are through the side of the inner thin sheets 208.

In assemblies using polymer microporous contactors, it is possible to use metal inner thin sheets and outer thin sheets, but bonding would be by clamping or bolting, relying on the polymer margin for sealing. Alternatively, the inner thin sheets and outer thin sheets may be a polymer as well wherein the entire assembly could be heat or chemically bonded.

Chemical Separations

Chemical separations as used herein includes any interfacial diffusion or exchange of a solute or working compound from one solvent or medium to another where the media may be liquid, gas, solid or combinations thereof. For example, in an absorption system a microporous contactor is selected so that a first medium contains the working compound and the second medium receives the working compound. One or the other or both of the media wet(s) the microporous contactor and the working compound transfers at an interface between the two media and through the microporous contactor. In a liquid—liquid extraction, one or both solvents may wet the microporous contactor. The boundary tension prevents mixing of the two media.

In the case of an adsorption system, the contactor may be a porous contactor, wherethrough the first medium (gas or liquid) passes and surrounds the second medium in the microplenum containing the second medium. The second medium is an adsorbent solid. During transient operation, such as during startup, the first medium may enter or leave the microplenum containing the second medium, but during steady state operation the first medium will be stagnant within the microplenum containing the second medium.

Absorber

When used as an absorber, a gas is introduced into cover 202 through inlet 210. A solute-weak solution (circulation fluid) enters the cover 204 through inlet 212 and the solute-strong solution exits through outlet 214. In the case wherein the absorber is part of an absorption heat pump, the solute or working compound is a refrigerant.

Rectifier and/or Analyzer

A rectifier and/or analyzer may be used to purify a stream for example to remove water vapor from a gaseous ammonia stream. Thus, it may have a mixed gaseous input stream, a purified gaseous output stream and a liquid output stream.

EXAMPLE 1

Figure 3:
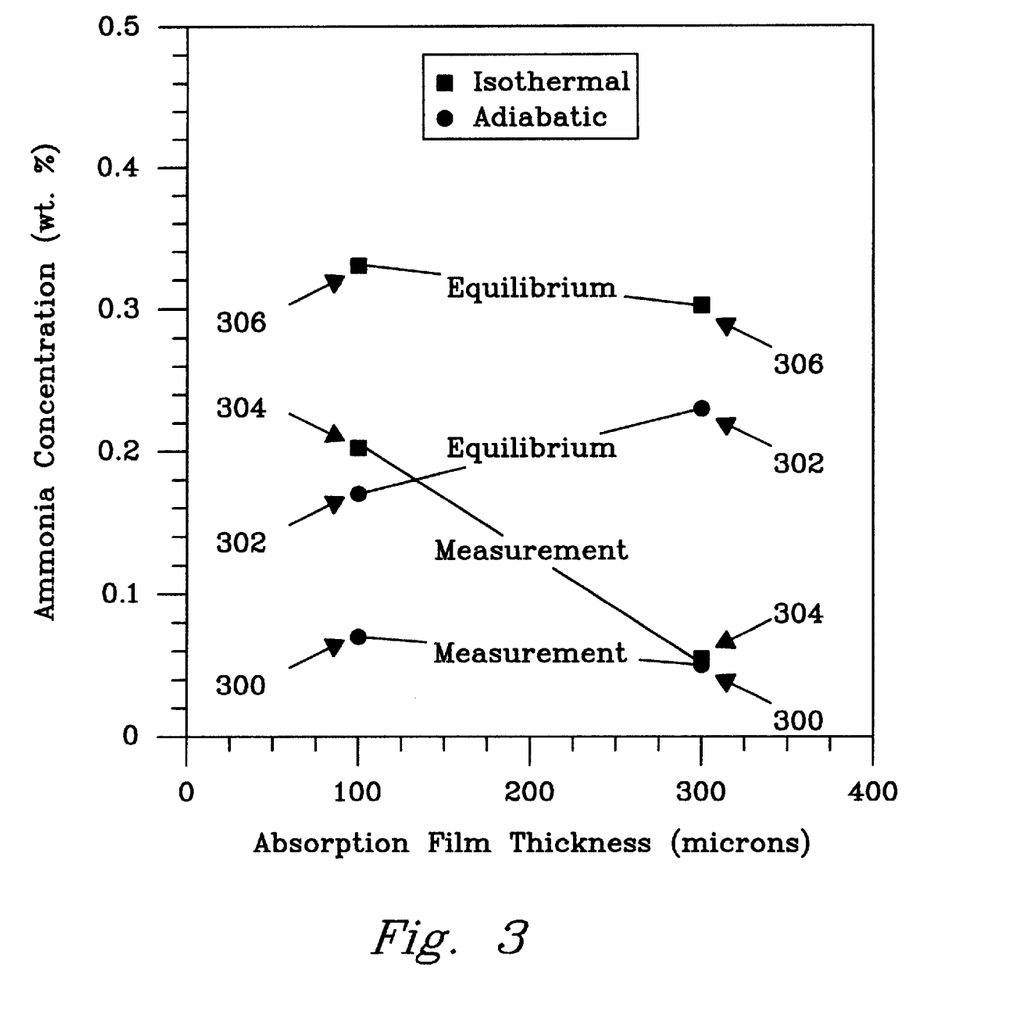
FIG. 3 is a graph of ammonia concentration versus absorption film thickness for Example 1.

An experiment was conducted to demonstrate separation in the form of gas absorption into a liquid. More specifically, ammonia vapor was absorbed into liquid water. A microporous contactor made of sintered stainless steel having a nominal thickness of 4 mm (1/16 inch), pore diameter range of from about 5 to about 30 micron and a porosity of from 30% to 50%. Cover sheets provided microplena having a thickness or distance from the microporous contactor sheet to the inside surface of the cover sheet (film thickness) ranging from about 100 to 300 microns. Within the liquid film on the microporous contactor, the ammonia was absorbed into the water. Ammonia flow rate varied from 0–4 g/min with water flow rate ranging from 0–33 g/min. Temperature ranged from 20–50° C. for isothermal and adiabatic test runs. Pressure in the absorber was from 15 to 30 psia. Data indicate that ammonia could be absorbed in water at a rate that generated between 10 and 30 W/cm$^2$. This absorption rate exceeds the performance of conventional absorbers by more than a factor of 10. Results are shown in FIG. 3. Considering first the measured data for the adiabatic test, the points 300 represent actual measurements of ammonia concentration at film thicknesses of 100 and 300 microns. The theoretical maximum absorption or "equilibrium" (which is a function of temperature) was calculated and represented by point 302 for the adiabatic test. As the absorption film thickness is decreased, the measured ammonia concentration approaches the theoretical maximum.

Similar results are shown for the isothermal test represented by actual measurement points 304 and equilibrium points 306. Had the test been truly isothermal, the equilibrium line would have been horizontal. The slight slope of that line indicates a difference in temperature at the different film thicknesses.

Comparing the adiabatic data and the isothermal data, it is clear that greater absorption is achievable with heat removal (isothermal) than with no heat removal (adiabatic).

Acid Gas Absorption

Absorption of an acid gas, for example carbon dioxide, hydrogen sulfide and combinations thereof is beneficial for cleaning up gas streams.

EXAMPLE 2

An experiment was conducted to demonstrate use of the microporous contactor unit of the present invention to absorb gaseous phase carbon dioxide ($CO_2$) into liquid diethanolamine (DEA) (gas-liquid absorption).

A polymer (Kapton) microporous contactor was made using a mask patterning process. A commercial excimer laser machine (Resonetics, Inc., Nashua, NH) had a rectangular beam profile (about 8 mm×about 25 mm) permitting multiple holes at a time to be made through a mask, significantly reducing overall machining time. Holes of 31 micrometer diameter spaced 61.5 micrometer in a 10 mm×80 mm matrix were made in about 20 minutes. The KrF excimer laser (248 nm) had a pulse energy of 257 mJ and pulse rate of 100 Hz was used.

The testing utilized the fluid film thickness of 400 microns on both sides of the 25-micron thick Kapton micromachined microporous contactor having 29–34 micron diameter holes and an active area of 1 by 8 cm. The DEA flow rate was held constant at 0.1 ml/min and the DEA concentration was varied from 0 to 40% (v/v of deionized water). The concentration of the gas was held constant at 20% $CO_2$ (v/v of $N_2$) and the gas flow rate was varied from 0.67 to 26.9 ml/min.

The results showed that as much as 99 to 100% of the $CO_2$ was absorbed. In a control, it was observed that only a small amount of $CO_2$ was absorbed by deionized water not containing any DEA.

Desorber

When a sorption unit is used as a desorber, a rich solution and circulating fluid enters the inlet. The rich solution is heated and the working compound leaves the circulating fluid via vaporization of the working compound and passes through the contactor to an outlet while the circulating fluid exits another outlet.

In an adsorption heat pump, the working compound is a refrigerant.

EXAMPLE 3

An experiment was conducted to demonstrate performance of a desorber according to the present invention.

Figure 4:
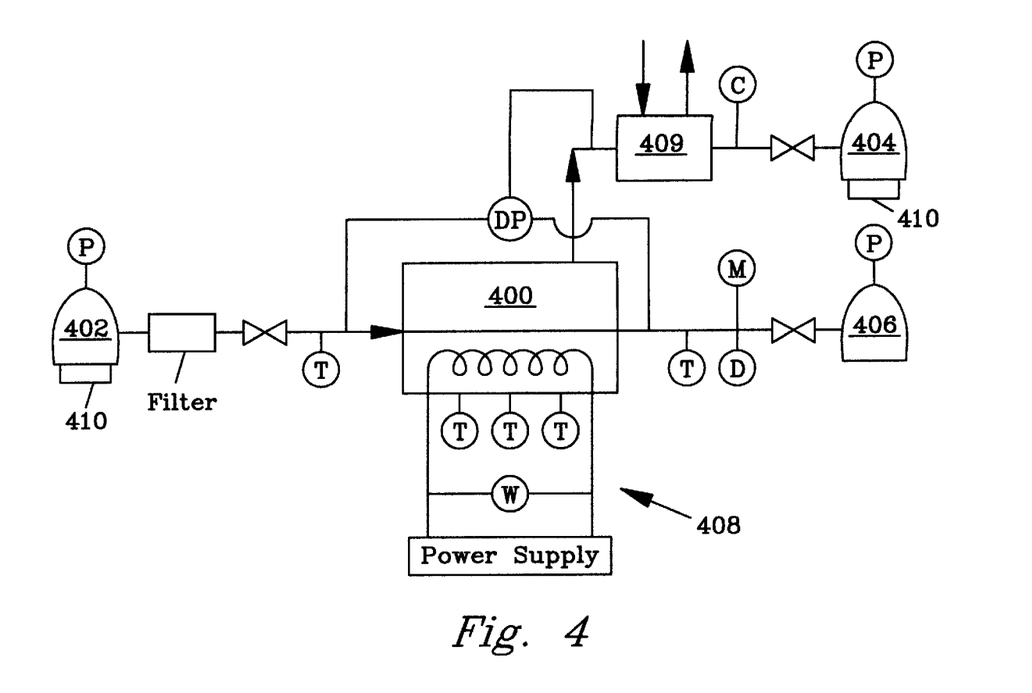
FIG. 4 is a schematic diagram of an experimental apparatus for demonstrating a liquid/gas desorber for Example 2.

$LiBr/H_2O$ was used. A diagram of the prototype test apparatus is illustrated in FIG. 4. The desorber 400 was a microporous contactor unit as shown in FIG. 2 plumbed between three reserviors 402, 404, 406. A resistance heater 408 was placed on the desorber 400. A vacuum pump (not shown) provided a pressure differential for fluid flow. A condenser 409 is used to capture the water vapor from the desorber 400. The low LiBr concentration reservoir 402 and the condensed water reservoir 404 were set on scales 410 for determining mass balance. Instrumentation included pressure sensors P, temperature sensors T, electric power sensor W, density sensor D, mass flow sensor M, conductivity sensor C, and differential pressure sensor DP.

Results show that water is desorbed from the solution at a rate of 0.3 g/cm$^2$/min. This exceeds the performance of conventional desorbers by a factor of 20.

Liquid—Liquid Extraction

When the microporous contactor unit (FIG. 2) used for solvent extraction, the solvent enters the cover 202 at inlet 210 and exits outlet 216. Feed enters inlet 212 and exits from outlet 214. For either absorption or liquid—liquid extraction, if heat must be removed or added, a microchannel heat exchanger sheet 218 may be used as shown.

When used as a chemical reactor, for example partial oxidation of liquid organics, the gas is oxygen that passes through the microporous contactor sheet 200.

EXAMPLE 4

Two experiments were conducted to demonstrate a microporous contactor unit for liquid—liquid solvent extraction. In the first, equilibrium concentration ratios were measured over a range of total solute concentrations to quantify the equilibrium partitioning coefficients for theoretical comparison. In the second, cyclohexanol was added to the water stream and cyclohexane was used as the extractant.

Two types of microporous contactors were used, micromachined and sintered plastic. Two thicknesses of plastic micromachined microporous contactors were used in the microchannel device. Plastic micromachined microporous contactors were fabricated by laser drilling a matrix of holes through Kapton polymeric 1-mil and 2-mil film (25-$\mu$m and 50-$\mu$m) covering an area 1-cm wide by 8-cm long. The holes are conical, averaging 25 $\mu$m in diameter on one side and 35 $\mu$m in diameter on the other side of the 25-$\mu$m-thickness films. Porosity was estimated at 26%. The plastic micromachined microporous contactors were coated with Teflon (polytetrafluoroethylene) to make them more non-wetting to water, giving higher breakthrough pressures.

For comparison to the performance of the plastic micromachined microporous contactors, experiments were performed with a Gelman 3-$\mu$m Zefluor PTFE (Teflon) microporous membrane as a plastic sintered microporous contactor. This plastic composite microporous contactor has a microporous Teflon layer approximately 15-$\mu$m thick mounted onto a 165-$\mu$m thick Teflon macroporous substrate, for a total thickness of 180 μm. The porosity of the 15-μm microporous layer is calculated to be 44%, based on void volume information obtained from Gelman. The plastic composite microporous contactor was consistently placed with the Teflon layer located toward the organic liquid side for all experiments.

The experiments were performed using a microporous contactor unit to distribute flow across the micromachined contactor plate or the microporous Teflon membrane at varying channel heights and flow rates. The channels in the housing or laminate were 10-cm long, 1-cm wide, and can be configured with various channel heights that can be different for the feed and solvent sides. In all experiments reported herein, the same channel heights were used on both sides of the microporous contactor and at equal flow rates. Channel heights used were 200 μm, 300 μm, 400 μm, and 500 μm. The plastic micromachined microporous contactors had 8 cm of active porous area, while the full 10 cm of channel length was utilized by the plastic composite microporous contactor.

A Harvard Apparatus, Model #22, syringe infusion pump was used to pump the liquids at constant flow rate through the microporous contactor unit. Pressure differential between the two liquid streams was measured in the tubing immediately downstream of the discharge ports of the microporous contactor unit using a water manometer. The water stream discharge pressure was kept slightly higher than the cyclohexane stream discharge pressure, though the pressure differential was generally less than an inch of water column.

Equilibrium partitioning coefficient data were collected by mixing a stock solution of 1000 mg/L cyclohexanol in water with cyclohexane in various volume ratios. The mixtures were allowed to equilibrate over several days. Samples were then taken from the water phase and analyzed by gas chromatography. The equilibrium partitioning data showed that, within the accuracy of the measurements, the partition coefficient was fairly constant over the range of total concentrations examined. An equilibrium partitioning coefficient of 1.3±0.2 was used in subsequent theoretical calculations.

Solvent extraction data were acquired with cyclohexanol as the extractant using three channel heights in the experiments with the plastic composite microporous contactor and one channel height with the plastic micromachined microporous contactor. Data for each were acquired sequentially by varying the flow rate with several purge volumes between extraction samples.

The tests with the plastic composite microporous contactor showed a significant improvement in performance when the flow channel heights were decreased from 400 μm to 300 μm, indicating appreciable mass transfer resistance in the flow channels at 400-μm channels. However, no discernible improvement was observed by decreasing the channel heights further to 200 μm, indicating the mass transfer resistance in the micropores dominates at this smaller channel height. The plastic micromachined microporous contactor performed at least as well as the plastic composite microporous contactor.

Adsorber

Figure 5:
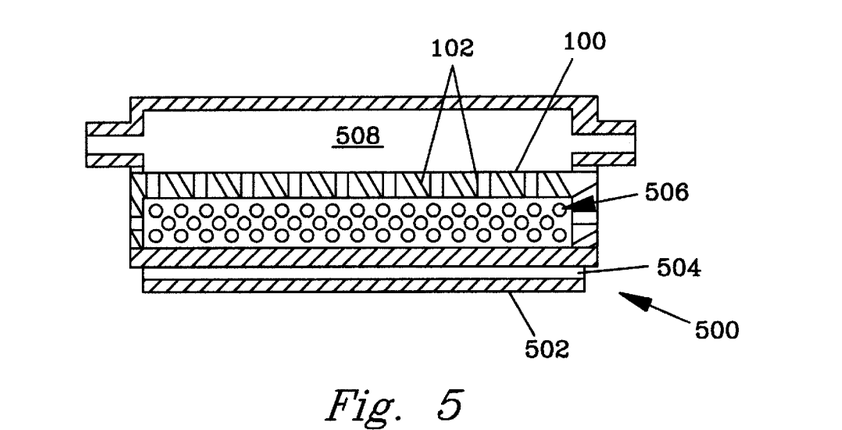
FIG. 5 is a cross section of a solid sorption cell.

The adsorbent of the adsorber may be any solid material capable of sorbing a gas. Carbon is a common adsorbent. In an adsorber, the solid adsorbent material strength and geometry is considered "boundary tension" as defined herein inasmuch as the material strength in combination with its geometry (size and shape) prevents its passage through the pores of the porous contactor. The individual solid sorbtion cell or stack, as shown in FIG. 5, consists of: 1) a microchannel heat exchanger 500 made of a 200 micron thick metal sheet 502 with microchannels 504, 2) a thin region (100 to 1000 microns) of adsorbent material (carbon) 506, 3) a porous contactor 100 that may be made by micromachining and 4) a fluid plenum 508.

When the fluid is a gas, during discharge (desorption), hot heat transfer fluid passes through the microchannels 504, heating the adsorbent 506 and therefore desorbing the gas. The gas passes through the pores 102 in the porous contactor 100 to the plenum 508 from which it exits the cell. The porous contactor 100 contains the adsorbent 506, even if it has crumbled into small particles during repeated cycling. Charging and discharging of the adsorbent may also be accomplished by pressure changes as well as by temperature changes.

During adsorption, the gas passes through the porous contactor 100 and diffuses into the adsorbent 506. A cooling fluid in the microchannel heat exchanger removes heat released during adsorption.

The inventory or amount of adsorbent is kept small by rapidly cycling the system while thermal cycling losses are minimized by keeping the thermal mass of the adsorption cell small. The adsorbent has an intial geometry of a geometric solid having a thickness of up to about 1 millimeter. The adsorbent is surrounded or enveloped by a pair of sheets or covers, at least one of which is a porous contactor that is porous or perforated for permitting mass diffusion therethrough to the adsorbent. The adsorbent achieves rapid mass transfer to and from the adsorbent, even if the adsorbent crumbles after repeated cycling and the adsorbent is effectively contained between the sheets.

Rapid cycling of the adsorbent is critical to downsizing or miniaturizing an adsorber. Microvalves for rapid actuation, microchannels for rapid (convective heat transfer coefficients of 1.0 to 2.0 $W/cm^2$-K and heat transfer rates up to 100 $W/cm^2$) heating/cooling of the adsorbent and mechanically constrained/contained thin film adsorber material cycling of the adsorbent from about 1 cycle per hour to about 1 cycle per second, or from about 10 cycles per hour to about 10 cycles per minute, preferably at least about an order of magnitude shorter cycle time than in the prior art. This reduces or minimizes the required inventory of the adsorbent. The low thermal mass of the system reduces or minimizes losses associated with thermal inertia.

When the adsorbent is an ion exchange resin, desorption of the solute may be effected through the introduction of an eluent chemical.

Microchannel Sorption Thermal Machine

Thermal machine as used herein includes any device that uses a working fluid for converting thermal energy (heat) to mechanical work or converting mechanical work to heat. Sorption thermal machine is a thermal machine that uses sorption to interact with the working fluid. An example is a thermochemical compressor. A thermochemical compressor in turn may be used with additional components to make an absorption cycle refrigeration system.

A microchannel sorption thermal machine is made by combining the porous contactor with a sorbent (absorbent or adsorbent) and a unit exchanging heat with the working fluid. The porous contactor may also be combined with a pressure machine for imparting or extracting work to or from the working fluid. A pressure machine is a pump, turbine, hydraulic ram or combination thereof.

EXAMPLE 5

Figure 6:
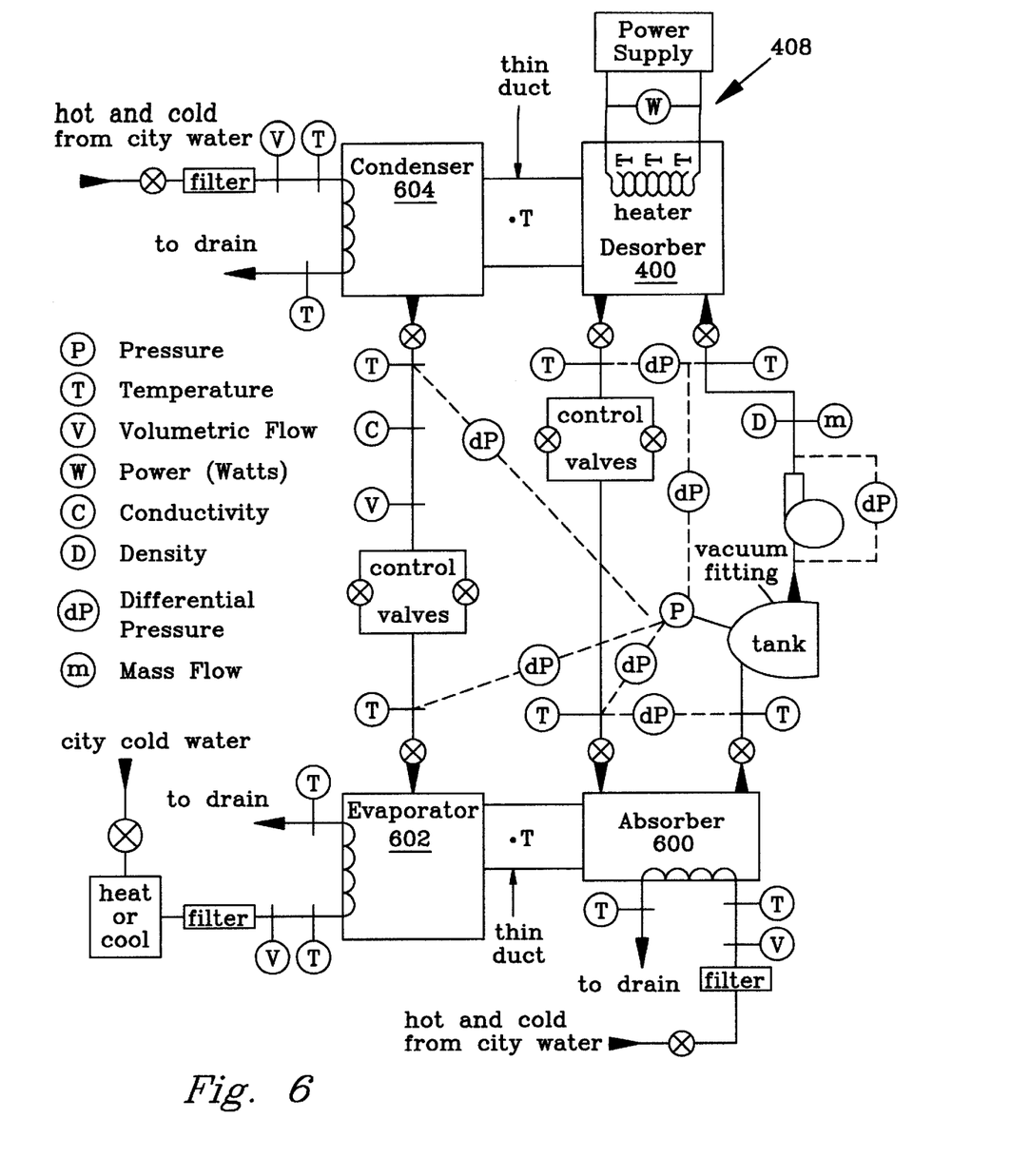
FIG. 6 is a schematic diagram of an experimental apparatus for demonstrating a microchannel absorption heat pump for Example 3.

An experiment is conducted to demonstrate a prototype absorption cycle heat pump according to the present invention. The experimental apparatus is illustrated in FIG. 6. The desorber 400, resistance heater 408, and instrumentation are substantially the same as in Example 2. The absorber 600 is of the same construction as the desorber 400 but cooled instead of heated. The condenser 604 and the evaporator 602 are of the same construction and are double-sided counterflow microchannel heat exchangers.

EXAMPLE 6

An experiment is conducted to demonstrate a prototype absorption cycle heat pump used as a cooler according to the present invention. Data from desorber and adsorber tests (Examples 1 and 2) together with computer simulation are herein used for prediction of the performance of a single-effect, LiBr/$H_2O$ absorption heat pump sized to provide 350 W of cooling. The system includes a water-cooled condenser and absorber, a water heat source for the evaporator, and a microchannel combustor with exhaust gas at 250° C. as the desorber heat source. In many applications, water cooling will be available (from the vehicle radiator for vehicle cooling and from a cooling tower for space conditioning). Other applications, such as manportable cooling, will require an air-cooled heat exchanger for ultimate heat rejection from the system.

The projected or simulation based weight and performance characteristics for two systems; one appropriate for manportable cooling applications and the other for vehicle or space conditioning applications. For manportable cooling applications, cooling water is assumed to have a temperature of 15° C. (60° F.), and a heat rejection temperature from the condenser of 46° C. (115° F.). For vehicle or space conditioning applications the cooling water is assumed to have lower temperature of 7° C. (45° F.) and a lower heat rejection temperature of 32° C. (90° F.). The two systems are nearly identical, with a total heat pump weight of approximately 650 g in a volume that is 1/60 the volume of a conventional LiBr heat pump, and a coefficient-of-performance (COP) of 0.68 for the manportable design and 0.71 for the space conditioning design. COP is the ratio of the amount of cooling provided divided by the thermal energy supplied to the desorber. For the manportable design, 1 W of heat provided by combusting fuel would provide 0.68 W of cooling. Electric power for pumping is reduced by a factor of 7 compared to vapor-compression heat pumps.

Adsorption Heat Pump

Figure 7:
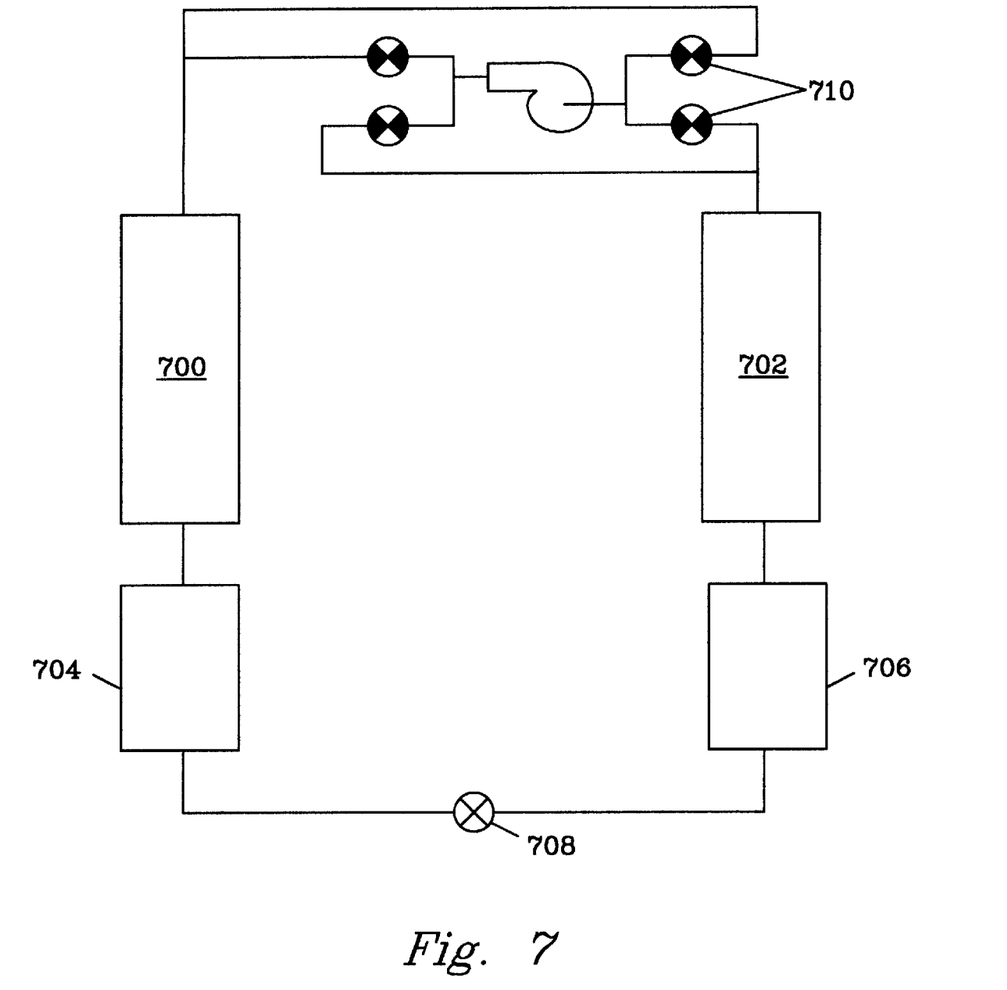
FIG. 7 is a schematic diagram of a solid sorption adsorption heat pump.

The porous adsorber described above is used with a refrigerant for the gas and additional components as shown in FIG. 7 to make an adsorption cycle heat pump according to the present invention. The microcomponent adsorption heat pump has two microchannel solid sorbent stacks 700, 702, two microchannel heat exchangers 704, 706 and an expander 708. Heat is supplied to the first solid sorbent stack acting as a desorber driving off the refrigerant from the solid sorbent. The refrigerant is cooled in one of the microchannel heat exchangers, expanded across pressure reduction valve 708, heated in the other of the microchannel heat exchangers and adsorbed in the second solid sorbent stack. The system may be fitted with valves 710 (conventional or microvalves) to allow the system to be reversed allowing desorption in the second stack and adsorption in the first stack. Alternatively, a reversible pump (not shown) may be used.

The solid sorbent stack may have one or many solid sorbent cells. It is preferred that a solid sorbent stack has many solid sorbent cells.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A porous contactor assembly for mass transfer of a working compound from a first medium to a second medium, comprising:
   (a) a porous contactor having a thickness, and further having a plurality of pores extending through the thickness, said pores of a geometry capable of cooperating with a boundary tension of one or the other or both of said first medium and said second medium to prevent migration of the one, the other or the both through said porous contactor and permitting passage of said working compound through said plurality of pores, said porous contactor placed between
   (b) a first laminate defining a first microplenum between said porous contactor and said first laminate for receiving said first medium, said microplenum having a depth less than a mass transfer boundary layer of said first medium; and
   (c) a cover sheet defining a second plenum between said porous contactor and said cover sheet for receiving said second medium.

2. The porous contactor assembly as recited in claim 1, wherein said plurality of pores is a plurality of micropores each having a cross section dimension from about 1 micron to about 30 micron as a microporous contactor assembly.

3. The microporous contactor assembly as recited in claim 2, wherein said first medium is a liquid.

4. The microporous contactor assembly as recited in claim 3, wherein said first medium is an aqueous solution, said second medium is a vapor or gas, wherein said aqueous solution is prevented from passing through said plurality of micropores and said working compound is permitted to pass therethrough, the microporous assembly selected from the group consisting of absorber, desorber, and combinations thereof.

5. The microporous contactor assembly as recited in claim 4, wherein said working compound is selected from the group consisting of acid gas, ammonia, water and combinations thereof.

6. The microporous contactor assembly as recited in claim 4, wherein said assembly comprises said first medium and said first medium is selected from the group consisting of aqueous lithium bromide, aqueous diethanolamine, aqueous ammonia and combinations thereof.

7. The microporous contactor assembly as recited in claim 3, wherein said assembly comprises said first medium that is a first liquid solvent and said second medium that is a second liquid solvent and said working compound that is a solute wherein said first solvent and said second solvent cooperate to form a boundary tension preventing flow of the first or second solvent through the microporous contactor but permitting contact of said first and second solvents within said plurality of micropores permitting said solute to transfer between said first and second solvents, the microporous contactor assembly is a liquid—liquid extractor.

8. A distillation unit comprising:
   (a) the microporous contactor assembly as recited in claim 3, wherein, during operation, said working compound is evaporated from a multicomponent liquid, said working compound passing through the microporous contactor; and
   (b) a second microporous contactor assembly as recited in claim 3, wherein said working compound is allowed to contact and condense within a multicomponent liquid, having the same constituents as said first multicomponent liquid.

9. The porous contactor assembly as recited in claim 2, wherein said micropores are substantially parallel oriented.

10. The porous contactor assembly as recited in claim 1, wherein said pores are randomly oriented.

11. The microporous contactor assembly as recited in claim 1, wherein said assembly comprises said working compound and said working compound is selected from the group consisting of carbon dioxide, hydrogen sulfide and combinations thereof.

12. The porous contactor assembly as recited in claim 1, wherein said assembly comprises said first medium that is an adsorbent solid prevented from passing through said plurality of pores and said second medium that is a fluid and said working compound that is a fluid constituent to be adsorbed or desorbed to or from said adsorbent solid, the porous assembly selected from the group consisting of adsorber, desorber and combinations thereof.

13. The porous contactor assembly as recited in claim 1, wherein said microplenum depth is less than or equal to about 500 micron.

14. The microcomponent assembly of claim 1 wherein the porous contactor is made using micromachining techniques.

15. The microcomponent assembly of claim 14 wherein the microporous contactor is made from plastic and the pores are formed using a laser.

16. The microcomponent assembly of claim 15 wherein the first microplenum has a thickness between 300 and 400 micrometers.

17. The porous contactor assembly of claim 1 wherein the first microplenum has a depth of about 1 micron to about 300 micron.

18. The porous contactor assembly of claim 1 further comprising projections or lands to support the porous contactor.

19. The porous contactor assembly of claim 1 wherein said second plenum is a microplenum.

20. An interfacial diffusion unit comprising:
a porous contactor assembly comprising
  (a) a porous contactor having a thickness, and further having a plurality of pores extending through the thickness, said pores of a geometry capable of cooperating with a boundary tension of one or the other or both of a first medium and a second medium to prevent migration of the one, the other or the both through said porous contactor and permitting passage of a working compound through said plurality of pores, said porous contactor placed between
  (b) a first laminate defining a first microplenum between said porous contactor and said first laminate for receiving said first medium, said microplenum having a depth less than a mass transfer boundary layer of said first medium; and
  (c) a cover sheet defining a second plenum between said porous contactor and said cover sheet for receiving said second medium and
a microchannel heat exchanger in contact with the porous contactor assembly.

21. A thermochemical compressor or desiccator, comprising:
  (a) the interfacial diffusion unit as recited in claim 20, where the working compound is a gas that is absorbed into a working fluid producing an absorbate, thereby giving up heat;
  (b) a pump for pressurizing the absorbate; and
  (c) a desorber comprising a microporous contactor assembly that comprises a liquid, and a vapor or gas wherein said liquid is prevented from passing through said plurality of micropores;
wherein heat is added and the vapor or gas is desorbed from the absorbate.

22. The thermochemical compressor or desiccator as recited in claim 21, further comprising:
  (d) a microchannel regenerative heat exchanger wherein heat is transferred from a desorber exit stream to a desorber inlet stream.

23. A microcomponent heat pump, comprising:
  (a) the thermochemical compressor as recited in claim 22 wherein said gas is a refrigerant;
  (b) a second microchannel heat exchanger for condensing the refrigerant;
  (c) an expander for reducing the pressure of the refrigerant; and
  (d) a third microchannel heat exchanger for evaporating the refrigerant.

24. An adsorption compressor, comprising:
  (a) an adsorber made from the interfacial diffusion unit as recited in claim 20; and
  (b) a desorber made from the interfacial diffusion unit as recited in claim 20; wherein
  (c) said adsorber and said desorber are operated cyclically with a gas as said working compound.

25. An adsorption heat pump, comprising:
  (a) the adsorption compressor as recited in claim 24, wherein said gas is a refrigerant;
  (b) a first microchannel heat exchanger for condensing the refrigerant;
  (c) an expander for decompressing the condensed refrigerant; and
  (d) a second microchannel heat exchanger for evaporating the decompressed and cooled refrigerant.

26. A sorption thermal machine, comprising:
  (a) a porous contactor placed between,
  (b) two covers wherein each cover has at least one microplenum facing the porous contactor, and
  (c) a pressure machine connected to the at least one microplenum for imparting or extracting mechanical work with respect to a fluid flowing therein.

27. The sorption thermal machine as recited in claim 26, wherein said porous contactor is a microporous contactor and one microplenum receives a liquid and another microplenum receives a gas.

28. An adsorption heat pump comprising the sorption thermal machine recited in claim 26.

29. An adsorber, comprising:
an adsorbent having an initial geometry of a geometric solid having a thickness of up to about 1 millimeter; and
a pair of sheets surrounding or enveloping said adsorbent in an adsorbent region that is 100 to 1000 microns thick, at least one sheet of said pair of sheets comprising a porous contactor for permitting mass diffusion of a working compound therethrough to said adsorbent; wherein
  said adsorbent achieves rapid mass transfer to and from the adsorbent, even if the adsorbent crumbles after repeated cycling and said adsorbent is effectively contained between said sheets.

30. The adsorber of claim 29 wherein at least one of said pair of sheets is metal.

31. The absorber of claim 29 in thermal contact with a microchannel heat exchanger.

32. A microcomponent assembly for mass transfer of a working compound from a first medium to a second medium, wherein either said first medium, said second medium or both is a liquid, the microcomponent assembly comprising:
  (a) a microporous contactor having a thickness, and further having a plurality of micropores extending through the thickness, said micropores of a geometry of a size and shape that a boundary tension of the liquid is capable of preventing migration of the liquid therethrough and permits passage of said working compound, said geometry is substantially the same for each of said plurality of micropores, said microporous contactor placed between
  (b) a first laminate such that a first space or first plenum is formed between said microporous contactor and said first laminate for receiving said first medium, said first plenum having a depth that is less than a mass transfer boundary layer of said first medium; and
  (c) a cover sheet such that a second space or second plenum is formed between said microporous contactor and said cover sheet for receiving said second medium.

33. The microcomponent assembly as recited in claim 32, wherein said plurality of micropores are substantially parallel to said thickness.

34. The microcomponent assembly as recited in claim 32, wherein said plurality of micropores are randomly oriented.

35. The microcomponent assembly as recited in claim 32, wherein said assembly comprises said first medium that is an aqueous solution, and said second medium that is a vapor or gas, wherein said aqueous solution is prevented from passing through said plurality of micropores and said working compound is permitted to pass therethrough, the microporous assembly selected from the group consisting of absorber, desorber, and combinations thereof.

36. The microcomponent assembly as recited in claim 35, wherein said working compound is selected from the group consisting of acid gas, ammonia, water and combinations thereof.

37. The microcomponent assembly as recited in claim 36, wherein said acid gas is selected from the group consisting of carbon dioxide, hydrogen sulfide and combinations thereof.

38. The microcomponent assembly as recited in claim 35, wherein said aqueous solution is selected from the group consisting of aqueous lithium bromide, aqueous diethanolamine, aqueous ammonia and combinations thereof.

39. The microcomponent assembly as recited in claim 32, wherein said assembly comprises said first medium that is a first liquid solvent and said second medium that is a second liquid solvent and a working compound that is a solute wherein said first solvent and said second solvent cooperate to form a boundary tension preventing flow of the first or second solvent through the microporous contactor but permitting contact of said first and second solvents within said plurality of micropores permitting said solute to transfer between said first and second solvents, the microporous contactor assembly is a liquid—liquid extractor.

40. The microcomponent assembly as recited in claim 32, wherein each of said plurality of micropores has a geometry of from about 1 micron to about 30 micron.

41. The microcomponent assembly as recited in claim 32, wherein said first plenum has a thickness of about 500 micron or less.

42. The microcomponent assembly of claim 32 wherein the microporous contactor is made from steel.

43. The microcomponent assembly of claim 42 wherein said micropores have diameters that range from about 5 to about 30 micrometers.

44. The porous contactor assembly of claim 32 wherein said second space or second plenum is a microplenum.

45. A contactor assembly comprising a first sheet, a porous contactor, and a second sheet;
  wherein said first sheet and said porous contactor define a first microplenum;
  wherein said second sheet and said porous contactor define a second microplenum; and
  wherein the first sheet, porous contactor and second sheet are essentially coplanar.

46. The contactor assembly of claim 45 wherein the porous contactor is microporous.

47. A heat exchanger in operative association with the assembly of claim 46.

48. The heat exchanger of claim 47 wherein the heat exchanger is a microchannel heat exchanger.

49. The microporous contactor assembly of claim 46 wherein said porous contactor comprises micromachined pores that have essentially no tortuosity.

50. The microporous contactor assembly of claim 46 made by bonding said first and second sheets, said porous contactor and first and second inner sheets;
  wherein the first inner sheet separates said first sheet and said porous contactor, and the second inner sheet separates said second sheet and said porous contactor;
  wherein said first and second inner sheets have openings; and
  wherein said first and second microplena are in said openings.

51. A contactor assembly comprising a fluid microplenum on at least one side of a microporous contactor sheet, combined with a microchannel heat exchanger.

52. The contactor assembly of claim 51 wherein the microchannel heat exchanger transfers heat to or from a fluid that can absorb or desorb.

\* \* \* \* \*